United States Patent [19]

Kondo et al.

[11] Patent Number: 4,812,398
[45] Date of Patent: Mar. 14, 1989

[54] REAGENT FOR MEASURING AMYLASE ACTIVITY AND MEASURING METHOD THEREOF

[75] Inventors: Hitoshi Kondo, Kyoto; Masao Kageyama, Joyo, both of Japan

[73] Assignee: Unitika Ltd., Hyogo, Japan

[21] Appl. No.: 861,306

[22] Filed: May 9, 1986

[30] Foreign Application Priority Data

May 9, 1985 [JP] Japan ................................. 60-98282

[51] Int. Cl.$^4$ .......................... C12Q 1/54; C12Q 1/40
[52] U.S. Cl. ........................................ 435/14; 435/15; 435/22
[58] Field of Search ............................. 435/22, 14, 15

[56] References Cited

U.S. PATENT DOCUMENTS

3,879,263  4/1975  Adams.
4,169,765  10/1979  Keyes ................................. 435/22

FOREIGN PATENT DOCUMENTS

0119722  9/1984  European Pat. Off. .
2630043  1/1978  Fed. Rep. of Germany .
2026692  2/1980  United Kingdom .

OTHER PUBLICATIONS

Biochemistry (Second Ed.), Chapt. 16, part 2, Albert Lehninger Worth Publishers.
Clinical Chemistry, vol. 27, No. 6, pp. 806-815. "Suitability of Control Materials for Determination of α-Amylase Activity".

Primary Examiner—Sam Rosen
Attorney, Agent, or Firm—Wenderoth, Lind & Ponack

[57] ABSTRACT

Disclosed is a reagent for measuring amylase activity in body fluids by cleaving an oligosaccharide having a defined chain length with amylase in body fluids to produce a glucose and measuring said glucose, characterized in that the reagent is divided to two portions, the first portion comprises an enzyme for converting a glucose and/or maltose naturally present in body fluids to glucose-6-phosphate, phosphoglucose isomerase, phosphofructokinase and adenosine-5'-triphosphate, and the second portion comprises said oligosaccharide being used as a substrate and a phosphoric acid ester of saccharides and/or saccharic acids; and a method for measuring amylase activity in body fluids comprising;
  eliminating glucose and/or maltose naturally present in body fluids with a first reagent comprising an enzyme for converting the glucose and/or maltose to glucose-6-phosphate, phosphoglucose isomerase, phosphofructokinase and adenosine-5'-triphosphate,
  adding a second reagent comprising a oligosaccharide substrate and a phosphoric acid ester of saccharides and/or saccharic acids to eliminate the phosphoglucose isomerase activity and to convert the oligosaccharide fragments formed by the action of amylase in body fluids to glucose by means of alpha-glucosidase or maltose phosphorylase, and measuring the amount of the obtained glucose.

9 Claims, No Drawings

REAGENT FOR MEASURING AMYLASE ACTIVITY AND MEASURING METHOD THEREOF

FIELD OF THE INVENTION

The present invention relates to a reagent for a measuring amylase activity of body fluids such as serum, urine and so on, and a measuring method thereof.

BACKGROUND OF THE INVENTION

Amylase is an enzyme present in body fluids such as saliva, pancreatic juice, urine, serum and so on. Amylase activity measurement is an important item in the field of a clinical examination for a diagnosis of pancreas diseases such as chronic or acute pancreatitis, pancreas cancer and the like; salivary glands diseases such as mumps and the like; renal insufficiency; chronic liver diseases; macroamylasemia; and the like.

The amylase activity has conventionally been measured by various methods and the reagents thereof. The methods can be classified in principle to the following four groups:

(1) Amyloclastic method utilizing starch-iodine reaction.

(2) Saccharogenic method which measures the amount of reducing saccharides formed from starch.

(3) Chromogenic method which measures free chromophores occurred from chromophore-bound starch.

(4) Turbidity process which measures turbidity by starch, especially amylopectin.

These four methods utilize starch or a polymeric amylose or amylopectin as a substrate, but it is difficult to obtain those having uniform quality. Also these methods have ambiguity in the relation between number of cleavage sites by amylase and actually measured values, which is an important defect. In addition, the method (1) indicates inferior analysis accuracy because the measurement is carried out by decrease in absorbance. In the method (2), a boiling treatment is inevitable and the degree of coloring is not constant in each produced cleavage site of oligosaccharide. In the method (3), the reaction period is long and a filtration or centrifuge treatment is necessary. Further, the method (4) is difficult for the substrate to be made uniform and the linear extent of the measured value is narrow.

A method in which amylase activity is measured using an oligosaccharide having a defined chain length as a substrate and a coupling enzyme and a reagent thereof have been recently proposed so as to obtain stoichiometrical relations between the number of cleavage sites by amylase and the measured value. The methods are classified to the following three:

(5) a method in which a substrate, i.e. an oligosaccharide having a defined chain length, is cleaved by amylase and then treated by a coupling enzyme such as alpha-glucosidase or maltose phosphorylase to form glucose, and the said glucose is determined by a conventional method (see U.S. Pat. No. 3879263, Japanese Patent Publication (unexamined) Nos. 37096/1978 and 19097/1980, and Japanese Patent Publication (examined) Nos. 33956/1982 and 33957/1982).

(6) a method in which a substrate, i.e. an oligosaccharide having a defined chain length, is cleaved by amylase to form maltose and said maltose is measured by a conventional method (see Japanese Patent Publication (unexamined) No. 80488/1979 and Japanese Patent Publication (examined) No. 27800/1980).

(7) a method in which a substrate, i.e. an oligosaccharide having a defined chain length bonded with p-nitrophenyl group or a substituted aromatic group (aglycone) in the reducing end through glycosidic bond, is cleaved by amylase and then allowed to be contacted to a coupling enzyme, such as glucosidase and the resultant free p-nitrophenyl or aglycone is measured by the absorption in the visible region (Japanese Patent Publication (unexamined) Nos. 25893/1979 and 2199/1985, and Japanese Patent Publication (examined) Nos. 53079/1982, 997/1984 and 13198/1984).

In the method (7), the developed color is unstable because it is changeable by pH, temperature and amount of the co-existent protein and the reproducibility is not so good. The substrate utilized in the method (7) is generally unstable in aqueous solution and it is late in cleaving rate by amylase in comparison with the corresponding oligosaccharide thereto. The method (7) is also complicated in the treatment of an inside standard material which needs to be used in the method (7).

In connection with the improvement of analysis accuracy, it has been found that amylase in body fluids is composed of salivary glands-derived amylase (hereinafter referred to as S) and pancreatic juice-derived amylase (hereinafter referred to as P). A substrate, therefore, is desired to have no difference in its reactivity between both amylases in order to measure the amylase activity in body fluids. In this context, E. Rauscher, U. Neumann, E. Schaich, S. von Buelow, and A. W. Wahlenfeld, Clin. Chem., 31. 14-19 (1985) reports that the oligosaccharide substituted by a substituent at a reducing end has larger P-activity/S-activity ratio than that of the corresponding aligosaccharide substrate. For example, the P-activity/S-activity ratio of p-nitrophenyl maltoheptaose is 1.72 to 1.77, while the P-activity/S-activity of maltoheptaose is 1.45 to 1.50. Maltopentaose has the P-activity/S-activity of 1.0, which is very valuable. Accordingly, in the measurement of the amylase activity in body fluids, the use of the oligosaccharide having a defined chain length as substrate is of value, and an application of it to the methods (5) and (6) is profitable in the clinical examination of amylase activity.

However, the methods (5) and (6) have a tendency to be measured higher than actual value, because glucose (called endogeneous glucose) or maltose (called exogeneous maltose which is recently employed in an intravenous drip) naturally existent in body fluids, especially serum or urine to be clinically examined, are also counted in the measured values according to the methods (5) and (6) wherein glucose and maltose are also produced as reaction intermediates. It is necessary to eliminate them from the body fluids in advance.

For eliminating endogeneous glucose or exogeneous maltose, column methods and enzymatic methods are proposed. In a utilizing the column method, body fluids are applied to a column such as gel filtration, but the column method is not acceptable to daily routine examinations because the operations are complicated.

The enzymatic methods are classified by enzymes being used. For example, Japanese Patent Publication (examined) Nos. 33956/1982 and 33957/1982 disclose that the elimination of endogeneous glucose and exogeneous maltose is carried out by alpha-glucosidase, hexokinase and glucose-6-phosphate dehydrogenase and lactate dehydrogenase. Japanese Patent Publication (unexamined) No. 19097/1980 discloses that oxamic acid makes inactive the above lactate dehydrogenase at the time of measuring amylse activity. Japanese Patent Publication (examined) No. 33958/1982 discloses that endogeneous glucose is removed with hexokinase and the activity of hexokinase is inactivated by an anionic surfactant such as alpha-olefin sulfonate at the time of measuring amylase activity. Further, Japanese Patent Publication (unexamined) No. 203500/1984 discloses that endogeneous glucose is eliminated with a system of mutarotase, glucose oxidase and catalase, and the catalase reaction is then stopped with sodium azide. However, prevention of the reaction to be stopped is not completely done and even high concentration of the above-described substance takes long time to stop the reaction. Also aberration of the measured value is often occurred in these enzymatic elimination methods.

As mentioned above, since the oligosaccharide having a defined chain length is the most suitable substrate for standerizing amylase activity because its cleavage sites are not varied so much depending on the pancreatic juice-derived amylase and the salivary glands-derived amylase and because the hydrolysis rate is rapid sufficient to be able to continuously follow up the reaction by means of Rate method, a method for measuring amylase activity in combination with an effective elimination method of endogeneous glucose or exogeneous maltose and a reagent thereof is strongly desirable to progress more effectively or constantly the method using the oligosaccharide having a defined chain length.

SUMMARY OF THE INVENTION

The present invention is to provide a method for measuring amylase activity combined with a system for fully eliminating endogeneous glucose or exogeneous maltose, and a reagent thereof. Surprisingly, it has been found as the result of studying various reagents and methods that efficiency in the elimination of endogeneous glucose or exogeneous maltose enhances by way of applying phosphoglucose isomerase and phosphofructokinase and that, at the time of measuring amylase activity, a phosphoric acid ester of saccharides and/or saccharic acids are added as an inhibitor for phosphoglucose isomerase activity to result in no adverse effect to amylase activity and the activity of the other coupling emzymes.

Thus, the present invention is to provide a for measuring amylase activity in body fluids by cleaving an oligosaccharide having a defined chain length with amylase in body fluids to produce a glucose and measuring said glucose, characterized in that the reagent is divided to two portions, the first portion comprises an enzyme for converting a glucose and/or maltose naturally present in body fluids to glucose-6-phosphate, phosphoglucose isomerase, phosphofructokinase and adenosine-5'-triphosphate, and the second portion comprises said oligosaccharide being used as a substrate and a phosphoric acid ester of saccharides and/or saccharic acids. The present invention also is to provide a method for measuring amylase activity in body fluids comprising;

eliminating glucose and/or maltose naturally present in body fluids with a first reagent comprising an enzyme for converting the glucose and/or maltose to glucose-6-phosphate, phosphoglucose isomerase, phosphofructokinase and adenosine-5'-triphosphate, adding a second reagent comprising a oligosaccharide substrate and a phosphoric acid ester of saccharides and/or saccharic acids to eliminate the phosphoglucose isomerase activity and to convert the oligosaccharide fragments formed by the action of amylase in body fluids to glucose by means of alpha-glucosidase or maltose phosphorylase, and measuring the amount of the obtained glucose.

The reagent of the present invention fully eliminates the interruption of endogeneous glucose or exogeneous maltose with the mesurement method of amylase activity to provide an improved accuracy of measuring amylase activity.

DETAILED DESCRIPTION OF THE PRESENT INVENTION

The reagent for measuring amylase activity in the body fluids of the present invention consists essentially of the first reagent relating to the elimination of endogeneous glucose and/or exogeneous maltose and the second reagent relating to a substrate of the enzyme reaction of amylase and to the inhibitor of phosphoglucose isomerase activity.

The first reagent contains alpha-glucosidase or maltose phosphorylase, glucokinase, phosphoglucose isomerase, phosphofructokinase and adenosine-5'triphosphate. Glucose-6-phosphate dehydrogenase may also be employed for the first reagent. It may further contain additives such as accelerators, stabilizer and the like. Examples of the additives are magnesium salts such as magnesium sulfate, magnesium acetate and the like; chlorides such as sodium chloride, potassium chloride and the like, calcium salts such as calcium chloride, calcium nitrate; thiol compounds such as N-acetylcysteine, glutathione, 2-aminoethylthiouronium bromide, thioglycolic acid, cysteine, mercaptoethanol, dithiothreitol, dithioerythritol and the like; sodium ethylenediaminetetraacetate (hereinafter referred to as EDTA); sodium azide as antiseptics; and the like. Examples of the stabilizers are proteins such as albumin, gamma-globulin and the like; water-soluble polymer compounds such as polyvinyl alcohol, polyethylene glycol and the like.

The above components are preferably dissolved in a buffer solution having pH 7.0 to 10.0. Examples of the buffer solutions are tris(hydroxymethyl)aminomethane (TRIS), triethanolamine, glycine, tris(hydroxymethyl)-methylglycine (TRICINE), N,N-bis(2-hydroxyethyl)glycine (BICINE), N-2-hydroxypiperadine-N'-2-ethanesulfonic acid (HEPES), 3-cyclohexylaminopropanesulfonic acid (CAPS) and the like, of which pH is adjusted within the range of 7.0 to 10.0. Preferred are TRIS, HEPES, TRICINE, BICINE. When maltose phosphorylase is used as a component of the first reagent, a phosphoric acid buffer may be used or contained as a substrate in the above-mentioned buffer solution.

The second reagent fundamentally contains an oligosaccharide substrate and a phosphoric acid ester of saccharides and/or saccharic acids. The second reagent may contain nicotinamide adenine dinucleotide (phosphate) (hereinafter referred to as NAD(P)). It may further contain the above-mentioned additives. Preferred oligosaccharide is those containing 4 to 8 degrees of polymerization of glucose in the chain. More preferred is maltopentaose. Examples of the phosphoric acid ester of saccharides and/or saccharic acids are erythrose-4-phosphate, 6-phosphogluconate, 5-phosphoarabinonate, 4-phosphoerythronate and a mixture thereof and the like. Preferred are erythrose-4-phosphate and 6-phosphogluconate because of their high inhibitory abilities against phosphoglucose isomerase activity, no adverse effects on amylase activity and the other coupling enzyme activities, safety and availability.

The above component is preferably dissolved in a buffer solution having pH 3.0 to 7.4. Examples of the buffer solutions are those adjusted pH to 3.0 to 7.4, such as imidazole, TRIS, triethanolamine, piperazine-N,N'-bis(2-ethanesulfonic acid) (PIPES), 3-(N-morphorino)-propanesulfonic acid (MOPS), 2-(N-morphorino)ethanesulfonic acid (MES), acetic acid, phosphoric acid buffer solution and the like. Preferred are imidazole, PIPES, MOPS, MES, and TRIS.

The amount of the above components of the present invention may be, for example, 1.0 to 300 unit/ml of alpha-glucosidase, 0.5 to 40 unit/ml of maltose phosphorylase, 0.1 to 40 unit/ml of glucokinase, 0.1 to 40 unit/ml of glucose-6-phosphate dehydrogenase, 0.1 to 40 unit/ml of phosphoglucose isomerase, 0.2 to 100 unit/ml of phosphofructokinase, 0.5 to 150 mM of adenosine-5'-triphosphate, 0.5 to 50 mM of an oligosaccharide having 4 to 8 degrees of polymerization of glucose, 0.05 to 20 mM of NAD(P), 0.5 to 30 mM of magnesium salts, 0.5 to 30 mM of chlorides, 0.05 to 30 mM of calcium salts, 0.5 to 50 mM of thiol compounds, 0.01 to 5.0% of stabilizers such as albumin, 0.5 to 50 mM of sodium azide, 0.01 to 100 mM of the phosphoric acid ester of saccharides and/or saccharic acids, or 1.0 to 100 mM of phosphate if maltose phosphorylase is employed. Preferred amount of them may be 2.0 to 150 unit/ml of alpha-glucosidase, 1.0 to 20 unit/ml of maltose phosphorylase, 0.2 to 20 unit/ml of glucokinase, 0.2 to 20 unit/ml of alucose-6-phosphate dehydrogenase, 0.2 to 20 unit/ml of phosphoglucose isomerase, 0.4 to 40 unit/ml of phosphofructokinase, 1.0 to 80 mM of adenosine-5'-triphosphate, 0.8 to 25 mM of an oligosaccharide having 4 to 8 degrees of polymerization of glucose, 0.1 to 10 mM of NAD(P), 1.0 to 20 mM of magnesium salts, 1.0 to 20 mM of chlorides, 0.1 to 15 mM of calcium salts, 1.0 to 25 mM of thiol compounds, 0.02 to 2.0% of stabilizers such as albumin, 1.0 to 30 mM of sodium azide, 0.05 to 50 mM of the phosphoric acid ester of saccharides and/or saccharic acids, or 2.0 to 50 mM of phosphate if maltose phosphorylase is employed.

The amounts of the first reagent and the second reagent are such that the pH of the system, when both reagents are mixed, is within the range of 6.0 to 7.2. Typical example of the ratio of the first reagent to the second reagent is 2:1 to 10:1 based on volume, preferably 2:1 to 8:1 based on volume. The concentrations of the buffers in the first reagent and the second reagent are easily selected when the other conditions are fixed. For example, when the ratio of the first reagent to the second reagent is 2:1, the pH of the first reagent is 8.0, the pH of the second reagent is 6.1 and the resultant solution pH is set 6.6 to 6.8, the concentration of the buffer in the first reagent falls in 35 mM of HEPES buffer solution (pH 8.0) and that in the second reagent falls in 120 mM of PIPES buffer solution (pH 6.1).

Glucokinase employed in the present invention is not limited in supply sources and may be those derived from microorganisms or those derived from animals. Preferred are those produced from microorganisms cultured at a most suitable growth temperature of 50° to 85° C. Examples of the microorganisms are Bacillus sp. such as *Bacillus stearothermophilus*, *Bacillus thermoproteolyticus*, *Bacillus acidocaldarius;* Thermoactinomyces sp.; Thermus sp; Thermomicrobium sp. and the like. Typical examples of the microorganisms are *Bacillus stearothermophilus*, of which specific examples are ATCC 7933 strain (ATCC; The American Type Culture Collection, Maryland, U.S.A.), ATCC 7954 strain, ATCC 10194 strain, ATCC 12980 strain, NCA 1503 strain (NCA; National Canners' Association, Washington, D.C., U.S.A.), UK 563 strain (FERM P-7275 strain, deposited at Fermentation Research Institute, Agency of Industrial Science and Technology, Ibaragi, Japan, on September 29, 1983) and the like.

Glucose-6-phosphate dehydrogenase is not limited in supply sources, like glucokinase, preferably those acting to not only NADP but also NAD as a coenzyme, such as derived from *Leuconostoc mesenteroides, Pseudomonas fluorescens.* More preferred are glucose-6-phosphate dehydrogenase derived from thermophilic microorganisms, which can act on both NADP and NAD and which is stable and has high preservability.

Phosphoglucose isomerase is not limited in supply sources, like glucokinase, and it can be those derived from animals such as rabbit muscles or those derived from microorganisms such as baker's yeast. Preferred are phosphoglucose isomerase derived from thermophilic microorganisms such as *Bacillus stearothermophilus* (NCA 1503 strain, 2184 strain and the like), which are stable and has high preservability.

Phosphofructokinase is not limited in supply sources, like glucokinase, and it can be those derived from animals such as rabbit muscles or those derived from microorganisms such as baker's yeast, brewer's yeast, Clostoridium sp., Escherichia sp., Bacillus sp., and the like. Preferred are phosphofructokinase derived from thermophilic microorganisms such as *Bacillus stearothermophilus* (NCA 1503 strain, 2184 strain and the like), which are stable and has high preservability.

Alpha-glucosidase is not limited in supply sources, like glucokinase, and it can be those derived from animals, plants or microorganisms. Preferred are those derived from microorganisms, such as yeasts, having substrate specificity of no function on oligosaccharides having larger glucose chain length than maltotetraoside.

Maltose phosphorylase is not limited in supply sources, like the above-mentioned enzymes. Preferred are those derived from Lactobacillus sp. such as *Lactobacillus brevis* and the like; and Neisseria sp. such as *Neisseria meningitidis* and the like.

Glucokinase, glucose-6-phosphate dehydrogenase, phosphoglucose isomerase, phosphofructokinase, alpha-glucosidase and maltose phosphorylase can be prepared from the above-described sources by an appropriate combination of known techniques in the art including extraction, purification, and so on.

In the measuring method of the present invention, the elimination of endogenous glucose and/or exogenous maltose can be carried out by the following two methods:

   (a)

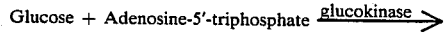

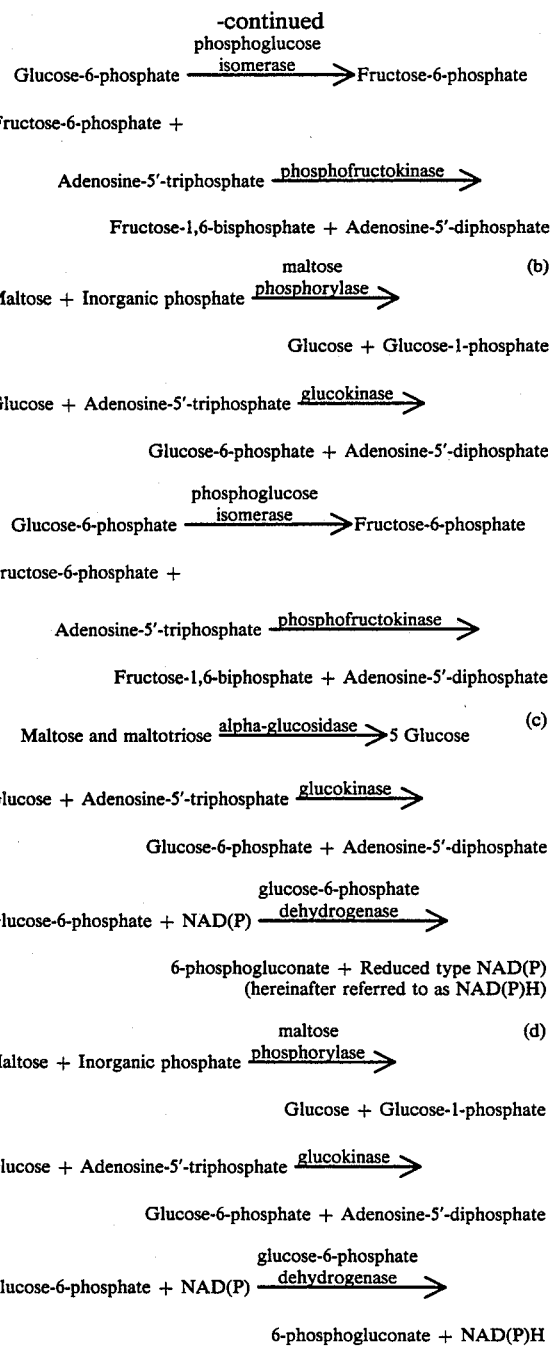

In this reaction, an increase in absorbance at 340 nm due to the formation of NAD(P)H is also measured.

Alpha-glucosidase and glucokinase are commonly employed in the combination of (a) and (c) and maltose phosphorylase and glucokinase are commonly employed in the combination of (b) and (d). When the combination of (a) and (d) or (b) and (c) is adopted, glucokinase is commonly employed.

Besides the reaction system (c) or (d), the glucose produced in the reaction system (c) or (d) is measured by well-known techniques, such as the reaction system of glucose oxidase-peroxidase, the reaction system of pyranoseoxidase-peroxidase, the reaction system of glucose dehydrogenase and the like. Also the glucose-1-phosphate produced in the reaction system (d) can be measured by using beta-phosphoglucomutase and glucose-6-phosphate dehydrogenase system. Further, these enzymes can be immobilized to membranes and the like and used a so-called enzyme electrode.

The present method is illustrated using maltopentaose as a substrate and alpha-glucosidase, i.e. the combination of (a) and (c). The first reagent is prepared by dissolving alpha-glucosidase, glucokinase, glucose-6-phosphate dehydrogenase, phosphoglucose isomerase, phosphofructokinase, adenosine-5'-triphosphate, potassium chloride, magnesium sulfate, calcium chloride, N-acetylcysteine, albumin, sodium azide, EDTA in a 35 mM of HEPES buffer solution (pH 8.0). A human serum or human urine is added to the first reagent to convert the glucose and/or maltose originally contained in the serum or urine to fructose-1,6-bisphospate accoding to the reaction system (a). The second reagent prepared by dissolving maltopentaose, NAD(P), erythrose-4-phosphate (or 6-phosphogluconate), and sodium azide in a 120 mM of PIPES buffer solution (pH 6.1) is added to the first reagent to stop the phosphoglucose isomerase activity immeadiately by the action of erythrose-4-phosphate (or 6-phosphogluconate). The amylase activity of the human serum or human urine is then measured according to the reaction system (c). This is similar to the combination of (b) and (d), (a) and (d), or (b) and (c) wherein maltose phosphorylase is used as a coupling enzyme. As mentioned above, the glucose produced by the amylase reaction-alpha-glucosidase system or the amylase reaction-maltose phosphorilase system is measured by the glucose oxidase-peroxidase reaction system, the pyranose oxidase-peroxidase reaction system, the glucose dehydrogenase reaction system and the like. The glucose-1-phosphate produced by the amylase reaction-maltose phosphorylase system can also be measured by the beta-phosphoglucomutase-glucose-6-phosphate dehydrogenase reaction system.

In the practice of the present invention, reaction temperature is preferably set within the range of 20° to 45° C. Reaction period is not limited, but the eliminating reaction of endogeneous glucose and/or exogeneous maltose by the first reagent is preferably carried out within 30 minutes. The shorter, the better for clinical examination. The reaction period for measuring amylase activity by the second reagent also is not limited, but it preferably ranges within 1 to 40 minutes.

The reagent and method of the present invention overcome the problem occurring from the existence of endogeneous glucose and/or exogeneous maltose in body fluids in case where the measurement of amylase activity is carried out using an oligosaccharide having 4 to 8 degrees of polymerization of glucose. According to the present invention, the endogeneous glucose and/or exogeneous maltose which disturbs an accurate measurement can be converted by the first reagent to a harmless substance in two minutes and the second reagent containing an oligosaccharide and a phosphoric acid ester of saccharides and/or saccharic acids is added to stop the phosphoglucose isomerase activity immediately and to simultaneouly measure the amylase activity in the body fluids. The measurement value of amylase activity is easily standardize and accuracy of the measurement enhances. The present invention is of value in application to clinical examination.

The present invention is illustrated by the following examples which should not be construed as limiting the present invention.

REFERENCE EXAMPLE 1

4.8 unit/ml of glucokinase, 3.6 unit/ml of phosphoglucose isomerase, 6.2 unit/ml of phosphofructokinase, 10 mM of adenosine-5'-triphosphate, 10 mM of N-acetylcystein, 10 mM of magnesium sulfate, 10 mM of potassium chloride, 5 mM of calcium chloride, 2 mM of EDTA were dissolved in a 50 mM of HEPES buffer solution (pH 8.2) to form a reagent.

One ml of the reagent was heated to 37° C., to which 10,000 mg/dl of a glucose solution was added to react and amounts of the remained glucose were measured after 1 minute, 1.5 minute, 2 minutes, 2.5 minutes by a determination kit of glucose (commercially available from Boehringer Mannheim Yamanouchi Co. Ltd.). The amount of the remained glucose was 4,200 mg/dl after 1 minute reaction, 1,100 mg/dl after 1.5 minutes reaction, 65 mg/dl after 2 minutes reaction, and 0 mg/dl after 2.5 minutes reation.

To the reagent was added 20 unit/ml of alpha-glucosidase derived from yeasts (commercially available from Boehringer Mannheim Yamanouchi Co. Ltd.) and a sufficient amount for 0.1% of a bovine serum albumin to form a maltose elimination reagent. One ml of the maltose elimination reagent was heated to 37° C. and 20 microliter of a 500 mg/dl maltose solution was added to react. The amounts of the remained maltose after 1 minute, 1.5 minute, 2 minutes and 2.5 minutes were measured using a determination kit of glucose commercially available after converting all of the remained maltose to glucose with alpha-glucosidase. It was found that the amount of the remained maltose was 205 mg/dl after 1 minute, 63 mg/dl after 1.5 minute, 11 mg/dl after 2 minutes and 0 mg/dl after 2.5 minutes. This shows that glucose and maltose is elimination in a short time even at a high concentration.

REFERENCE EXAMPLE 2

For a comparison, 6.0 unit/ml of hexokinase (derived from yeasts; Boehringer Mannheim Yamanouchi Co. Ltd.), 10 mM of adenosine-5'-triphosphate, 10 mM of N-acetylcysteine, 10 mM of magnesium sulfate, 10 mM of potassium chloride, 5 mM of calcium chloride, 2 mM of EDTA were dissolved in a 50 mM of HEPES buffer solution (pH 8.2) to form a reagent.

One ml of the reagent was heated to 37 ° C., to which 10,000 mg/dl of a glucose solution was added to react and amounts of the remained glucose were measured after 1 minute, 2 minutes, 3 minutes, 4 minutes, 5 minutes and 10 minutes by a determination kit of glucose (commercially available from Boehringer Mannheim Yamanouchi Co. Ltd.). The amount of the remained glucose was 7,300 mg/dl after 1 minute reaction, 5,200 mg/dl after 2 minutes reaction, 3,700 mg/dl after 3 minutes reaction, 2,200 mg/dl after 4 minutes, 1,300 mg/dl after 5 minutes, and 10 mg/dl after 10 minutes reation.

EXAMPLE 1

According to Archives of Biochemistry and Biophysics 144, 245 (1971), phosphoglucose isomerase was purified from *Bacillus stearothermophilus* NCA 1503 strain through microorganism disruption, ammonium sulfate fractionation, polyethylene glycol treatment, DEAE-cellulose (available from Whatman Ltd.) chromatography, Sephadex G-200 (available from Pharmacia Fine Chemicals) chromatography, and DEAE-cellulose rechromatography. Phosphofructokinase was purified from *Bacillus stearothermophilus* NCA 1503 strain according to FEBS Letters, 55, 282 (1975) through a microorganism disruption, DEAE-cellulose chromatography, DEAE-Sephadex (available from Pharmacia Fine Chemicals) chromatography and AMP-Sepharose (available from Pharmacia Fine Chemicals) chromatography. Maltose phosphorylase was also purified from *Lactobacillus brevis* ATCC 8287 strain according to Agricultural and Biological Chemistry, 37, 2813 (1973) through microorganism disruption, ammonium sulfate fractionation, DEAE-cellulose chromatography, and hydroxyapatite (available from Wako Pure Chemical Industries, Ltd.) chromatography.

A first regent was prepared by adding 20 unit/ml of alpha-glucosidase, 4.8 unit/ml of glucokinase (derived from *Bacillus stearothermophilus*; available from Seikagaku Kogyo Co. Ltd., 3.6 unit/ml of phosphoglucose isomerase, 6.2 unit/ml of phosphofructokinase, 1.8 unit/ml of glucose-6-phosphate dehydrogenase (derived from *Leuconostoc mesenteroides*; available from Oriental Yeast Co., Ltd.), 10 mM of adenosine-5'-triphosphate, 10 mM of N-acetylcysteine, 10 mM of magnesium sulfate, 10 mM of potassium chloride, 5 mM of calcium chloride, 2 mM of EDTA, and 0.1% by weight of a bovine serum albumin to a 35 mM of HEPES buffer solution (pH 8.0). A second reagent was prepared by adding 9.0 mM of maltopentaose (available from Nakarai Chemicals Ltd.), 6.0 mM of NADP, 10 mM of 6-phosphogluconate (available from Oriental Yeast Co., Ltd.) to a 120 mM of PIPES buffer solution (pH 6.1).

The measurement of amylase activity was made at 37° C. as follows: Five samples of serum were prepared by respectively adding 8,000 mg/dl, 4,000 mg/dl, 2,000 mg/dl, 1,000 mg/dl of glucose and adding nothing for blank. Another five samples of urine were prepared similar to the serum samples. 500 microliter of the first reagent mentioned above was poured in a glass cuvette having the optical path length of 1 cm and 10 microliter of serum or urine samples was added and maintained at 37° C. for 2 minutes. 250 microliter of the second reagent was then added and maintained at 37 ° C. The amylase activity was measured by an absorbance change at 340 nm using a spectrophotometer.

The initial absorbance ($OD_{340}$) right after the addition of the second reagent and the amylase activity in the serum samples were respectively 0.212, 132.8 unit/l; 0.225, 132.8 unit/l; 0.217, 132.0 unit/l; 0.220, 132.3 unit/l; and 0.218, 132.1 unit/l. These values of the urine samples were respectively 0.278, 212.4 unit/l; 0.268, 222.0 unit/l; 0.284, 215 unit/l; 0.276, 214.0 unit/l; and 0.280, 218.0 unit/l.

Another serum sample containing 400 mg/dl of maltose was prepared and measured as generally described above. The initial absorbance and amylase activity were respectively 0.227, 131.6 unit/l.

As seen above, the reagent of the present invention can eliminate glucose and maltose at a high concentration in a short time and make possible an accurate measurement of amylase activity.

COMPARATIVE EXAMPLE 1

For a comparison, a first and second reagent were prepared as generally described in Example 1 with the exception that phosphoglucose isomerase and phosphofructokinase, were not added to the first reagent and same measurement was carried out.

A serum sample containing 1,000 mg/dl of glucose had the initial absorbance of 1.429 and the amylase activity of 145.5 unit/l. A serum sample containing 2,000 mg/dl of glucose had initial absobance beyond the scale of the spectrophotometer, which shows impossible to measure. A urine sample containing 1,000 mg/dl was merely possible to measure and indicated the initial absorbance of 1.480 and the amylase activity of 246.4 unit/l. Also a serum sample containing 400 mg/dl of maltose had the initial absorbance of 1.167 and the amylase activity of 141.5 unit/l.

As shown above, glucose and maltose were not completely eliminated without phosphoglucose isomerase and phosphofructokinase and the values measured were varied widely.

COMPARATIVE EXAMPLE 2

For a comparison, a first and second reagent were prepared as generally described in Example 1 with the exception that 6-phosphogluconate was not added to the second reagent and the same measurement was carried out. The initial absorbance and amylase activity were respectively 0.218, 115.1 unit/l; 0.215, 114.5 unit/l; 0.210, 116.2 unit/l; 0.216, 114.8 unit/l and 0.218, 115.5 unit/l.

Accordingly, where 6-phosphogluconate was not added, a part of the glucose produced by the amylase reaction and alpha-glucosidase reaction were eliminated to lower the measured value of amylase activity.

EXAMPLE 2

A first reagent and a second reagent were prepared as generally described in Example 1 with the exception that 8 unit/ml of maltose phosphorylase is used instead of alpha-glucosidase and 50 mM of sodium phosphate was additionally added to the first reagent, and that pH of the first reagent was adjusted to 7.5 and that pH of the second reagent was adjusted to 6.5. Serum samples employed were the same as Example 1. In serum samples containing glucose, the initial absorbance and amylase activity were respectively 0.225, 132.5 unit/l; 0.218, 133.8 unit/l; 0.225, 131.9 unit/l; 0.222, 133.1 unit/l; and 0.218, 132.1 unit/l. In a sample containing maltose, the initial absorbance and amylase activity were 0.228, 133.5 unit/l.

This example shows an advantage of the present invention at the point that amylase activity was accurately measure with no relation to an amount of glucose and maltose in body fluids.

COMPARATIVE EXAMPLE 4

For a comparison, a reaction system using hexokinase was studied.

A first reagent was prepared by adding 6.0 unit/ml of hexokinase, 20 unit/ml of alpha-glucosidase, 100 unit/ml of glucose oxidase (derived from Aspergillus niger; available from Boehringer Mannheim Yamanouchi Co., Ltd.), 2.0 unit/ml of mutarotase (derived from hog kidney; available from Boehriger Mannheim Yamanouchi Co., Ltd.), 500 unit/ml of catalase (derived from bovine liver; available from Boehriger Mannheim Yamanouch Co., Ltd.), 0.7 mM of 4-aminoantipyrine, 10 mM of adenosine-5'-triphosphate, 10 mM of sodium chloride, 5 mM of calcium chloride, and 10 mM of magnesium sulfate to a 35 mM of HEPES buffer solution (pH 8.0). A second reagent was prepared by adding 15 unit/ml of peroxidase (derived from horse radish; Boehringer Mannheim Yamanouchi Co., Ltd.), 3 mM of maltopentaose, 10 mM of sodium chloride, 5 mM of calcium chloride, 10 mM of phenol, 0.5 mM of sodium acetate and 4% by weight of alpha-olefin sulfonate to a 120 mM of PIPES buffer solution (pH 6.1).

Measurement was carried out by the absorbance at 505 nm as generally described in Example 2. Additionally, a standard sample having a known amylase activity was employed to obtain its amylase activity. The serum sample containing 2,000 mg/dl of glucose had amylase activity of 110.1 unit/l, which shows that inhibition of the hexokinase activity is not sufficient by alpha-olefin sulfonate.

EXAMPLE 3

A first reagent and second reagent were prepared as generally described in Example 1 with the exception that 0.8 mM of erythrose-4-phosphate was employed instead of 6-phosphogluconate in the second reagent.

As the result, in serum samples containing glucose, the initial absorbance and amylase activity were respectively 0.215, 131.3 unit/l; 0.218, 132.5 unit/l, 0.212, 131.6 unit/l; 0.214, 130.5 unit/l; and 0.218, 132.1 unit/l. In a serum sample containing maltose, the initial absorbance and amylase activity were 0.220, 130.8 unit/l.

The present example also illustrates that amylase activity was accurately measured in spite of amounts of glucose and maltose.

What is claimed is:

1. A reagent for measuring amylase activity in body fluids by cleaving an oligosaccharide having a defined chain length with amylase in body fluids to produce a glucose and measuring said glucose, characterized in that the reagent is divided into two portions, the first portion comprises an enzyme for converting a glucose and/or maltose naturally present in body fluids to glucose-6-phosphate, and also containing phosphoglucose isomerase, phosphofructokinase and adenosine-5'-triphosphate, and the second portion comprises said oligosaccharide being used as a substrate and a phosphoric acid ester of saccharides and/or saccharic acids.

2. The reagent of claim 1 in which the enzyme for converting glucose is glucokinase.

3. The reagent of claim 1 in which the enzyme for converting maltose or both a maltose and a glucose is a combination of either maltose phosphorylase or alpha-glucosidase with glucokinase.

4. The reagent of claim 2 in which glucokinase is derived from microorganisms having an optimum growth temperature of 50° to 85° C.

5. The reagent of claim 3 in which glucokinase is derived from microorganisms having an optimum growth temperature of 50° to 85° C.

6. A method for measuring amylase activity in body fluids comprising;
   eliminating glucose and/or maltose naturally present in body fluids with a first reagent comprising an enzyme for converting the glucose and/or maltose to glucose-6-phosphate, and also containing phosphoglucose isomerase, phosphofructokinase and adenosine-5'-triphosphate,
   adding a second reagent comprising a oligosaccharide substrate and a phosphoric acid ester of saccharides and/or saccharic acids to eliminate the phosphoglucose isomerase activity and to convert the oligosaccharide fragments formed by the action of amylase in body fluids to glucose by means of alpha-glucosidase or maltose phosphorylase, and measuring the amount of the obtained glucose.

7. The method of claim 6 wherein the enzyme for converting glucose in the first reagent is glucokinase.

8. The method of claim 6 wherein the enzyme for converting maltose or both a maltose and a glucose in the first reagent is a combination of either maltose phosphorylase or alpha-glucosidase with glucokinase.

9. The method of claim 6 wherein glucokinase is derived from microorganisms having an optimum growth temperature of 50° to 85° C.

* * * * *